United States Patent [19]

Gäde

[11] 4,214,167
[45] Jul. 22, 1980

[54] DEVICE FOR PROTECTION OF THE GONADS

[76] Inventor: Ernst-August Gäde, Annastrase 10, Limburg, Fed. Rep. of Germany

[21] Appl. No.: 937,862

[22] Filed: Aug. 29, 1978

[30] Foreign Application Priority Data

Sep. 1, 1977 [DE] Fed. Rep. of Germany ... 7727061[U]

[51] Int. Cl.² ............................................... G21F 3/00
[52] U.S. Cl. ..................................... 250/515; 250/456
[58] Field of Search ............... 250/515, 516, 519, 451, 250/452, 456

[56] References Cited
U.S. PATENT DOCUMENTS

| 3,649,835 | 3/1912 | Brackenbrough et al. | 250/515 |
| 3,723,743 | 3/1973 | Brackenbrough et al. | 250/515 |
| 3,944,838 | 3/1976 | Gade | 250/515 |

Primary Examiner—Bruce C. Anderson
Attorney, Agent, or Firm—Craig & Antonelli

[57] ABSTRACT

A device for protection of gonads in x-ray diagnosis is disclosed. The device comprises a retaining frame for fastening to the collimator of an x-ray diagnosis instrument by means of insert strips. The retaining frame receives a movable support strip of material that is permeable to x-rays and which supports a member of material that is impermeable to x-rays. Insert strips for fastening the retaining frame to a collimator of an x-ray instrument are disposed on the retaining frame so as to be movable with respect to each other so that the protective device can be fastened to different x-ray diagnosis instruments.

7 Claims, 2 Drawing Figures

DEVICE FOR PROTECTION OF THE GONADS

BACKGROUND AND SUMMARY OF THE INVENTION

The present invention is directed to a device for protection of the gonads in x-ray diagnosis comprising a retaining frame which can be fastened onto the collimator of an instrument for x-ray diagnosis by means of a pair of parallel insert strips, which presents two opposed retaining slots serving to receive a movable support strip made of material that is permeable to light and x-rays, that supports a plate made of material that is impermeable to light and x-rays.

The proposed device finds application in instruments for x-ray diagnosis of any kind insofar as they are equipped with a collimator.

A protective device for the gonads is known from German Offenlegungsschrift No. 2,406,717, which can be disposed on the collimator of an instrument for x-ray diagnosis. This device with which the endangered gonads can be simply shielded, comprises a lead plate let into a support strip, said strip being movably disposed in a retaining frame fixed to the collimator. Fastening is effected by means of insert strips with U-shaped cross section that constitute part of the retaining frame, said strips being insertable in grooves provided on the collimator. Since the separation between these grooves is different in various x-ray apparatus, it has been necessary thus far to have a protective device of specific size for each instrument for x-ray diagnosis, and for this reason such devices thus far have been relatively expensive and have been introduced slowly.

An object of the present invention is to overcome the aforementioned disadvantages associated with this known protective device and to provide an improved protective device for the gonads which has universal applicability in instruments for x-ray diagnosis of various structural types.

These and other objects of the present invention are attained according to a preferred embodiment of the present invention by providing in a known device of the aforementioned type insert strips on the retaining frame which are disposed so as to be opposedly movable. As a result of this arrangement, a single form of the present invention can be utilized on all instruments for x-ray diagnosis that come into question and concomitantly the manufacturing cost is reduced substantially. The new universal applicability of the present invention offers the go-ahead for introduction of this important protective instrument.

According to the preferred embodiment of the present invention parallel slots are provided on the retaining frame, for movement of the insert strips. These slots allow disposition of guide and clamping members for the insert strips.

As a further feature of the preferred embodiment, prismatic guide tips extend at the foot of the insert strips, engaging in the slots. The guide tips facilitate the movement of the insert strips and ensure that the strips will remain parallel to each other during insertion.

To fix the insert strips in the desired position, set screws are disposed on the foot of the insert strips, their shanks passing through the slots. The insert strips can be clamped to the retaining frame by these set screws.

According to another feature of the invention, there can be two parallel retaining bridge members between the slots on the retaining frame. These bridge members considerably facilitate the use of the device because by means of these members support strips as required may be inserted in the retaining frame in two perpendicular directions.

The above and other objects, features and advantages of the present invention will become more apparent from the description of a preferred embodiment set forth hereinafter when considered in conjunction with the accompanying drawings wherein the same reference numerals are used to designate like parts throughout the several views.

Figure 1:
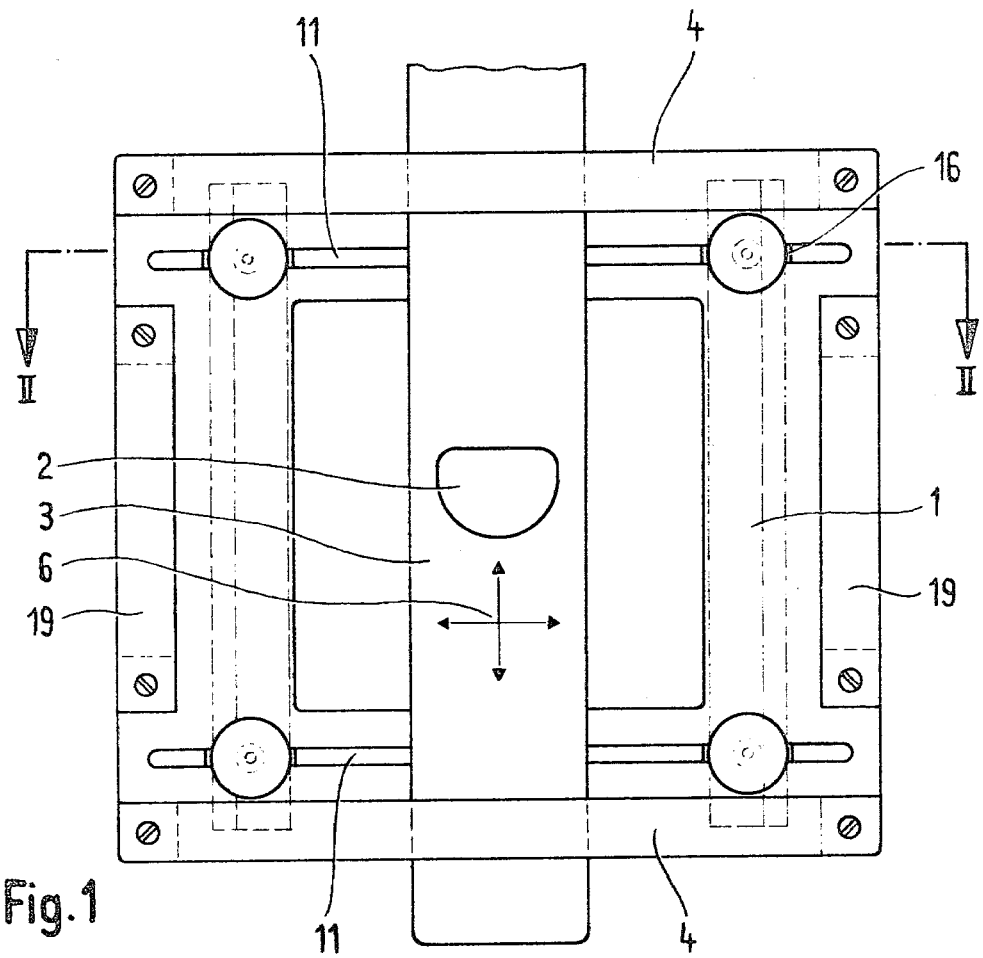
FIG. 1 is a bottom view of a device for protection of the gonads according to the present invention.

A device shown in FIG. 1 for protection of the gonads in x-ray diagnosis comprises a nearly rectangular retaining frame 1, advantageously made of a suitable plastic, as well as a support strip 3 which supports a plate 2.

The plate 2 is made of a substance which is impermeable to light and x-rays, e.g. lead, while the support strip 3 is made of a material such as acrylic glass which is permeable to light and x-rays. Plate 2, having a configuration adapted to the female or male gonads to be protected, is embedded in support strip 3.

Two retaining plates 4 are screwed onto retaining frame 1 at their ends while inwardly therefrom the plates are spaced at a distance corresponding to the thickness of the support strip from the retaining frame, forming two opposed retaining slots 5 in which support strip 3 can be inserted. By moving support strip 3, as indicated by arrows 6, with respect to retaining frame 1, when the collimator of the x-ray apparatus (not shown) is switched on, plate 2 will be brought to the place where the gonads are shielded from the x-rays.

Two parallel insert strips are provided for fastening the retaining frame 1 to the x-ray instrument. The two parallel insert strips are inserted into grooves 8 provided for them in the collimator 9 of the x-ray instrument indicated by dashed lines in FIG. 2.

Figure 2:
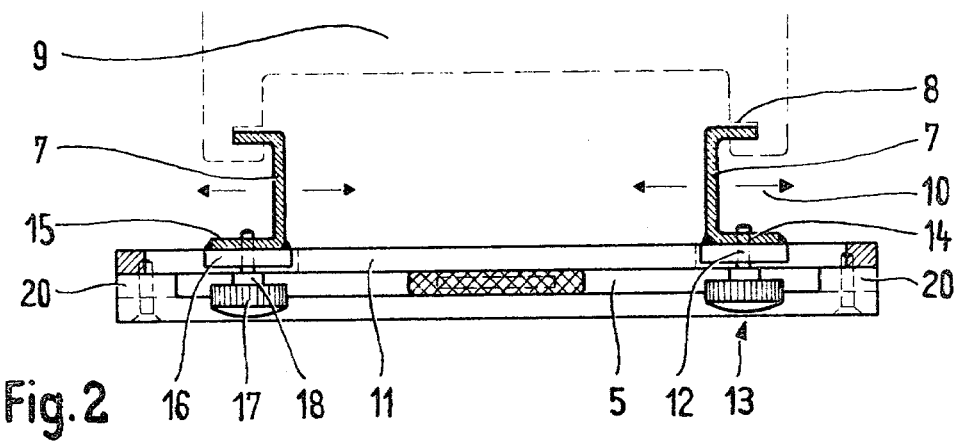
FIG. 2 is a cross-sectional view of the device of FIG. 1 taken along line II-II of FIG. 1.

The two insert strips 7 are disposed so that they are movable with respect to each other on retaining frame 1, as indicated by arrows 10 in FIG. 2. Two parallel slots 11 are provided on retaining frame 1, through which the shanks 12 of two set screws 13 for each strip 7 engage, turning in thread 14 on foot 15 of insert strips 7.

The height of insert strips 7 can be so selected that the device can be clamped on an area-dose potentiometer.

On foot 15 of insert strips 7, there are prismatic guide tips 16 that engage in slots 11. The said guide tips 16—see FIG. 2—are welded or hard-soldered on the U-profiled insert strips 7, which are made of sheet steel. The height of guide tips 16 is somewhat less than the thickness of retaining frame 1 so that, by means of a collar 18 on the underside of head 17 of set screws 13, there can be fixed clamping of insert strips 7 at the desired location.

Two retaining bridge members 19 are also provided on retaining frame 1 between slots 11 so that support strips can be selectively inserted crosswise.

While I have shown and described only one embodiment in accordance with the present invention, it is understood that the same is not limited thereto but is susceptible of numerous changes and modifications as known to those skilled in the art, and I therefore do not wish to be limited to the details shown and described herein but intend to cover all such changes and modifications as are encompassed by the scope of the appended claims.

I claim:

1. In a device for protection of gonads in x-ray diagnosis comprising a retaining frame for fastening to the collimator of an x-ray diagnosis instrument by means of insert strips, said retaining frame having means for receiving a movable support strip of material that is permeable to x-rays and which supports a member of material that is impermeable to x-rays, the improvement comprising said retaining frame being provided with a plurality of insert strips for fastening said retaining frame to said collimator, said insert strips being disposed on the retaining frame so as to be movable with respect to each other so that the protective device can be fastened to different x-ray diagnosis instruments,
   wherein said plurality of insert strips includes a pair of parallel insert strips,
   wherein said pair of parallel insert strips are disposed on the retaining frame along a pair of parallel slots, said pair of insert strips being movable with respect to each other along said slots,
   wherein portions of said pair of parallel insert strips adjacent said retaining frame are provided with prismatic guide tips which engage in said slots, and
   wherein set screws are provided for securing said pair of parallel insert strips to said retaining frame, the shanks of said set screws projecting through said slots and engaging in threads provided in said pair of parallel insert strips.

2. The device for protection of gonads according to claim 1, wherein the means for receiving a movable support strip in said retaining frame includes two opposed retaining slots for receiving the movable strip and wherein two parallel retaining bridge members are provided on the retaining frame between said slots so that the support strip can be selectively inserted crosswise.

3. The device for protection of gonads according to claim 1, wherein said member is a plate having a configuration adapted to the female or male gonads to be protected.

4. A device for protection of gonads in x-ray diagnosis comprising a retaining frame for fastening to the collimator of an x-ray diagnosis instrument by means of insert strips, said retaining frame having means for receiving a movable support strip of material that is permeable to x-rays and which supports a member of material that is impermeable to x-rays, a plurality of insert strips for fastening said retaining frame to said collimator and means disposing said insert strips on said frame so that the relative position of said insert strips with respect to each other can be adjusted whereby the protective device can be fastened to different x-ray diagnosis instruments.

5. The device according to claim 4, wherein said plurality of insert strips includes a pair of parallel insert strips and said retaining frame includes a pair of parallel slots, said pair of insert strips being adjustably positioned with respect to each other along said slots by said means disposing the insert strips on the frame.

6. The device according to claim 5, wherein portions of said pair of parallel insert strips adjacent said retaining frame are provided with prismatric guide tips which engage in said slots.

7. The device according to claim 4, wherein the means for receiving a movable support strip in said retaining frame includes two opposed retaining slots for receiving the movable strip and wherein two parallel retaining bridge members are provided on the retaining frame between said slots so that the support strip can be selectively inserted crosswise.

* * * * *